US00PP24807P3

(12) United States Plant Patent
Wheeler et al.

(10) Patent No.: US PP24,807 P3
(45) Date of Patent: Aug. 26, 2014

(54) BLUEBERRY PLANT NAMED "BB05-251MI-14"

(50) Latin Name: *Vaccinium corymbosum*
Varietal Denomination: BB05-251MI-14

(71) Applicant: Berry Blue, LLC, Grand Junction, MI (US)

(72) Inventors: Edmund J. Wheeler, Holland, MI (US); James F. Hancock, East Lansing, MI (US)

(73) Assignee: Berry Blue, LLC, Grand Junction, MI (US)

( * ) Notice: Subject to any disclaimer, the term of this patent is extended or adjusted under 35 U.S.C. 154(b) by 43 days.

(21) Appl. No.: 13/653,272

(22) Filed: Oct. 16, 2012

(65) Prior Publication Data

US 2014/0109271 P1 Apr. 17, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP9,834 | P | 3/1997 | Lyrene |
| PP10,675 | P | 11/1998 | Lyrene |
| PP11,807 | P2 | 3/2001 | Lyrene |
| PP11,829 | P2 | 4/2001 | Lyrene |
| PP12,165 | P2 | 10/2001 | Lyrene |
| PP15,103 | P3 | 8/2004 | Hancock |
| PP15,146 | P3 | 9/2004 | Hancock |
| PP16,333 | P3 | 3/2006 | Lyrene |
| PP16,404 | P3 | 4/2006 | Lyrene |
| PP18,138 | P3 | 10/2007 | Nesmith |
| PP19,503 | P3 | 11/2008 | Lyrene |
| PP20,027 | P3 | 5/2009 | Lyrene |
| PP21,881 | P3 | 4/2011 | Patel |
| PP22,692 | P3 | 5/2012 | Nesmith |
| PP22,778 | P3 | 6/2012 | Wright et al. |

*Primary Examiner* — Annette Para
(74) *Attorney, Agent, or Firm* — Graybeal Jackson LLP

(57) ABSTRACT

A new and distinct cultivar of blueberry plant named 'BB05-251MI-14' as described and shown herein. 'BB05-251MI-14' is a new and distinct high chill tetraploid Northern highbush blueberry (*Vaccinium*) variety of ancestry based largely on *V. corymbosum* with a limited number of genes from *V. angustifolium*. It is a productive late season variety that ripens approximately at the same time as Liberty, and 21 days after Bluecrop. 'BB05-251MI-14' provides a very good yield potential, a very good plant vigor, fruit quality and firmness, as well as mechanical harvest potential, and very good flavor and texture.

3 Drawing Sheets

BACKGROUND AND SUMMARY

Blueberries are a well-known fruit enjoyed by many throughout the world. One example of an existing, patented blueberry variety is Bluecrop, unpatented. Another example of an existing, patented blueberry variety is Elliott, also unpatented.

Compared to Bluecrop, 'BB05-251MI-14', has a medium upright bush shape compared to a spreading shape for Bluecrop. Also, Bluecrop's mean harvest date is 3 weeks before the harvest date for 'BB05-251MI-14', and 'BB05-251MI-14' has a larger berry size, a much firmer berry, and a very long storage compared to Bluecrop.

Compared to Elliott, Elliott has a more spreading bush shape than 'BB05-251MI-14', and Elliott is 7 days later. The fruit size for 'BB05-251MI-14' is much larger than Elliott and Elliott has smaller and a more narrow leaf shape compared to 'BB05-251MI-14'.

The present cultivar, 'BB05-251MI-14', provides one or more advantages compared to these and/or other blueberry varieties.

BRIEF DESCRIPTION OF THE PHOTOGRAPHS

DETAILED DESCRIPTION

Figure 1:
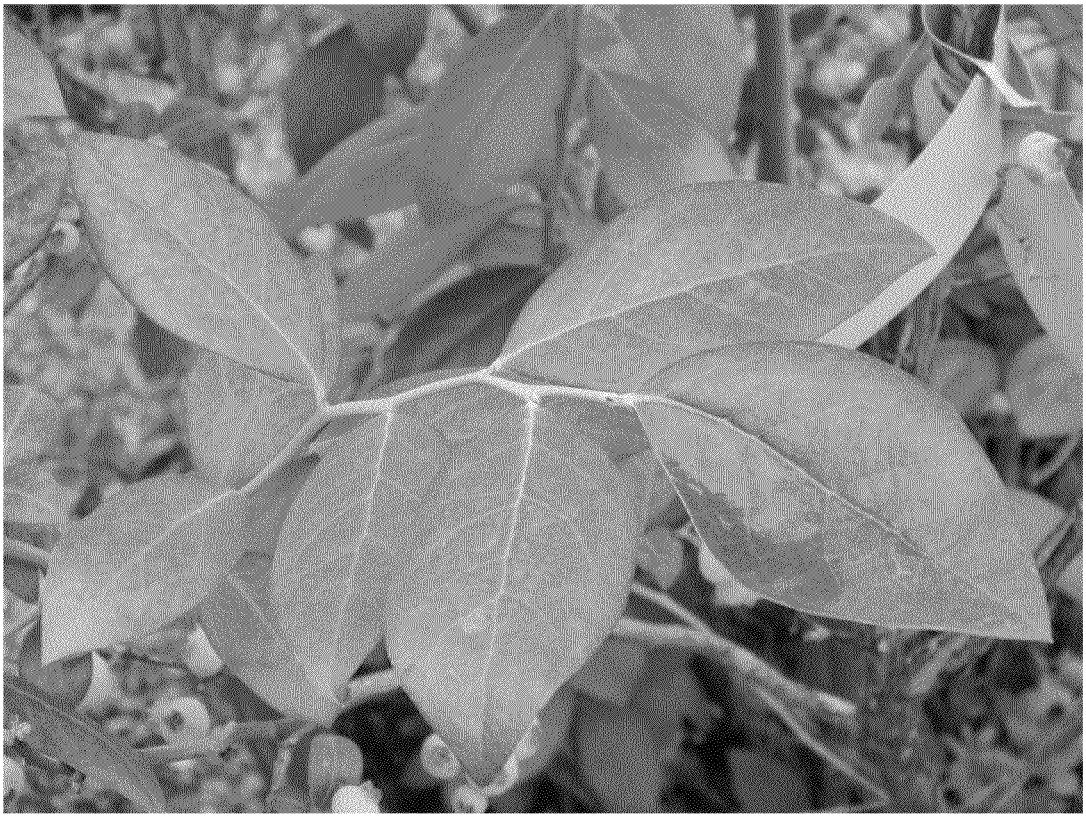
FIG. 1 is a close-up photograph taken in July 2012 of the Blueberry cultivar 'BB05-251MI-14', showing mature leaves that show the shape, coloration, venation, petiole length and color, and internode length of the variety.
Figure 2:
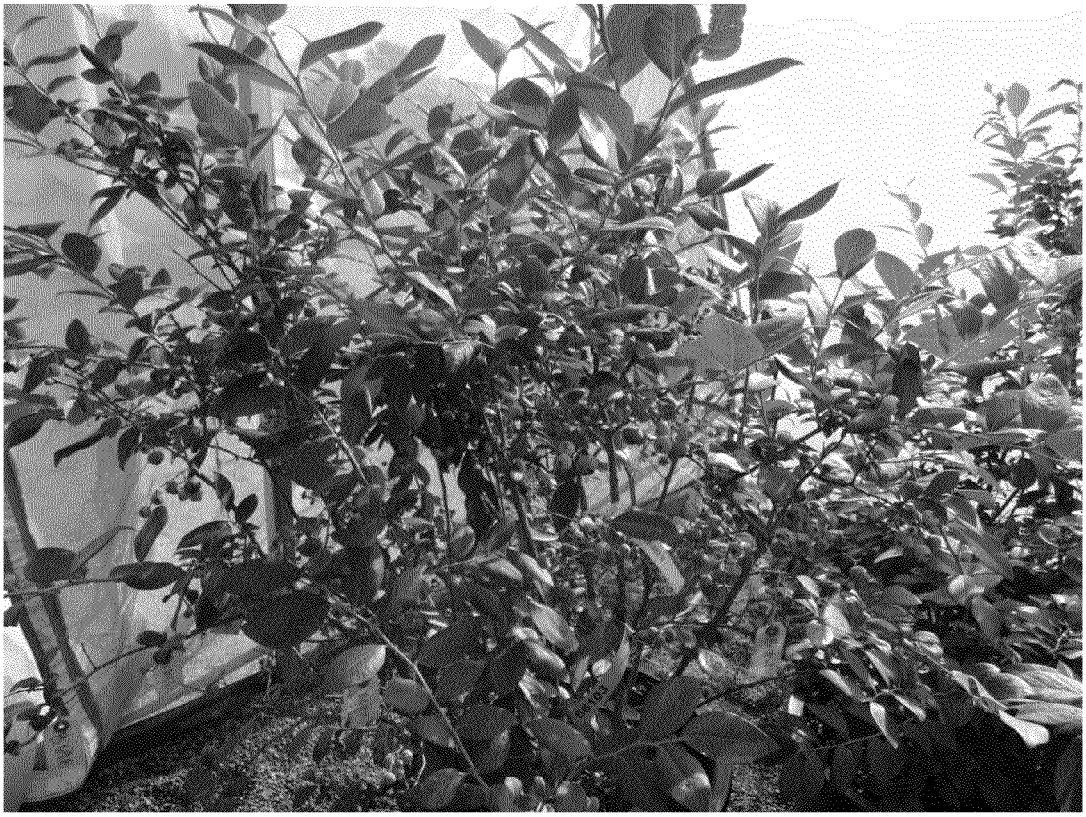
FIG. 2 is a photograph taken in July 2012 of the Blueberry cultivar 'BB05-251MI-14', showing a potted mature bush that shows the bush shape, branching pattern, fruit clusters and fruit presentation of the variety.
Figure 3:
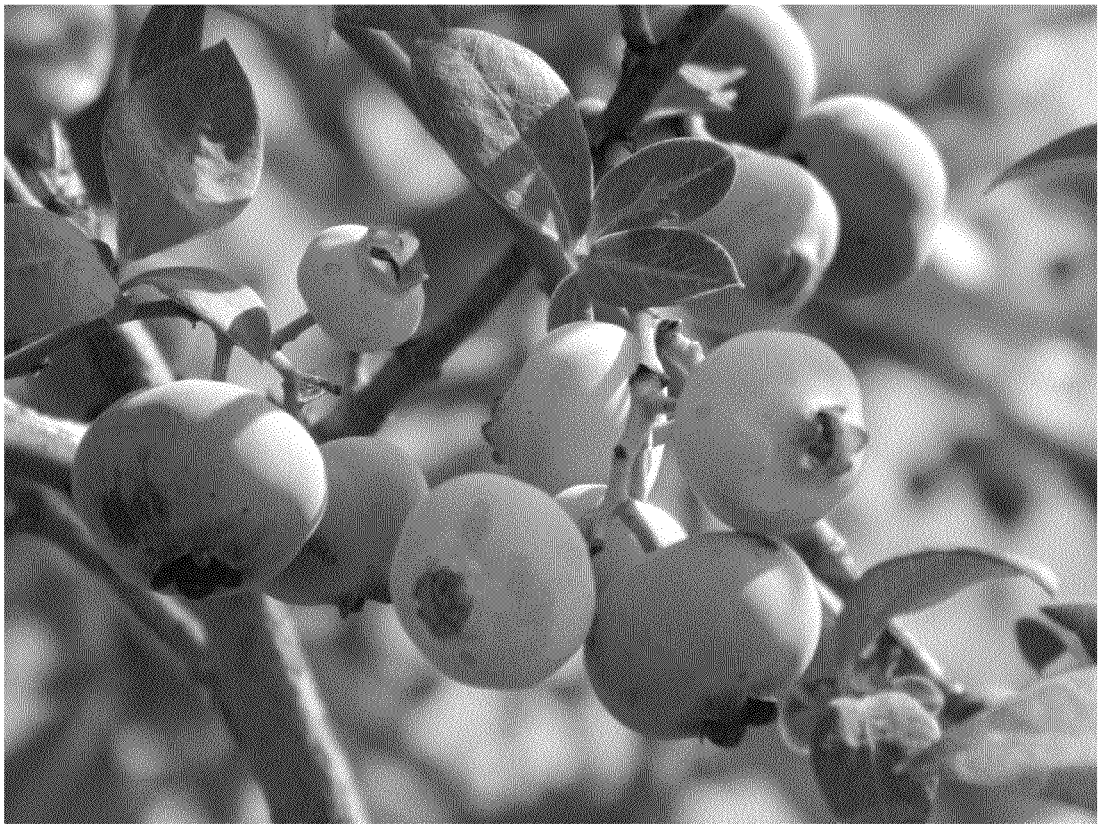
FIG. 3 is a close-up photograph taken in July 2012 of the Blueberry cultivar 'BB05-251MI-14', showing a fruit cluster with ripe and unripe fruit, and also showing cluster density, pedicel attachment, peduncle, fruit shape and calyx size.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Grand Junction in 2011 and 2012. Data were obtained on plants that were 6 years old.

Cultivar name: 'BB05-251MI-14'.

Classification:

*Family*.—Ericaceae.

*Botanical name*.—*Vaccinium corymbosum*.

*Common name*.—Blueberry.

Parentage:

*Female parent*.—Name: Liberty (Brigitta unpatented× Elliott unpatented). U.S. Plant Pat. No. 15,146. Compared to Liberty, 'BB05-251MI-14' has a maturity date that is 3-5 days earlier. 'BB05-251MI-14' has a slightly rounder berry shape and darker blue color than Liberty. 'BB05-251MI-14' also has a slightly larger size berry and much firmer berry compared to Liberty.

*Male parent*.—Nelson (Bluecrop unpatented×G107 unpatented). U.S. Plant Pat. No.: none. Compared to Nelson, 'BB05-251MI-14' matures 7 to 10 days later. 'BB05-251MI-14' has a slightly larger and much firmer berry than Nelson. 'BB05-251MI-14' has a slightly darker blue color, and much improved storage ability compared to Nelson. Also, Nelson has much more spreading bush shape than 'BB05-251MI-14'.

'BB05-251MI-14' was created from a cross in a greenhouse in South Haven, Mich., in 2005. Emasculated flowers of Liberty were hand pollinated with pollen from Nelson. Seed was sown, germinated, and plants were grown for 18 months and then planted in a seedling evaluation plot near Muskegon, Mich. in 2007. The plant was evaluated for 3 years and first selected in 2010, based on its excellent and desirable fruit and morphological characteristics—maturity date, bush habit, berry quality, flavor, and storage ability. The bush was dug from the field in October 2011 and transplanted into a pot and placed in a virus-free screened greenhouse. Additional plants have been propagated by softwood cuttings and tissue culture. The plants propagated have retained the original characteristics. Five and ten bush advanced trials have been planted in Grand Junction, Gobles, South Haven, and Muskegon, Mich. in 2011 and 2012.

'BB05-251MI-14' was first asexually propagated from softwood cuttings in 2011 in Grand Junction, Mich. The cuttings were rooted from the selected plant and several times since as desired. Micropropagation by tissue culture was also first initiated in 2011 and produced 200 cloned plants. The propagated plants from softwood cuttings and tissue culture have retained the original characteristics. This variety roots readily from softwood cuttings and tissue culture microshoots.

Field observations were made in 2012 on a mature 6-year old plant located in Grand Junction, Mich. Laboratory analysis of fruit characteristics were also done in Grand Junction.

General comments: 'BB05-251MI-14' is a new and distinct high chill tetraploid Northern highbush blueberry (*Vaccinium*) variety of primarily *V. corymbosum*, with a limited number of genes from *V. angustifolium*, from the breeding program of Berry Blue LLC. It is a productive mid-late season berry that ripens between Bluecrop and Elliott, two widely planted cultivars. It is characterized as having large fruit, medium light blue in color, very firm with a very small and dry picking scar. The fruit is well exposed on a vigorous medium upright bush. Along with a small crown, a loose fruit cluster, concentrated ripening, very firm and easily detachable fruit, the variety displays characteristics suitable for mechanical harvest. It is intended for areas that successfully grow high chill Northern highbush varieties. Ripe fruit are large, typically between 2.5-3 grams/berry. The mean date of flowering in southern Michigan is May 1. Frost protection may be needed for successful pollination and fruit set. Winter chill requirement for successful flowering and leafing is at least 1000 hours below 7° C. Flowering and leafing are synchronous. The mean ripening date is about July 28. Fruit shape is oblate with a medium high amount of waxy bloom that is persistent following handling. 'BB05-251MI-14' has excellent yield, mechanical harvest characteristics, extended storage ability, flavor and quality.

References to color refer to The Pantone Book of Color, Eisemann and Herbert, Harry N. Abrams, Inc. Publishers, New York, ISBN 0-8109-3711-5, 1990.

SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Firmness readings—BioWorks FirmTec2, Wamena, Kans.

Average size information: Medium large bush, medium upright shape, 6-year old plant 120 cm height, 115 cm width, height/width ratio 1:1.

Growth: Very good.

Productivity: Very good.

Cold hardiness: Leaf and flower buds −26° C., open flowers and fruit −2° C.

Specific features of the variety:

Plant:

*Growth habit*.—Medium upright.

*Plant width*.—90 cm.

*Plant height*.—120 cm.

*Spread*.—115 cm.

*Productivity*.—6-7 lbs per mature bush.

*Cold hardiness/tolerance*.—Leaf and flower buds −26° C., flowers and fruit −2° C.

*Chilling requirement*.—1000+ hours below 7° C.

*Canes*.—Modestly branched, 8-9 canes/bush, 40-50 cm range, average 44 cm; medium number of laterals.

*Mature cane color*.—Pantone Gray Sand 13-1010.

*Texture*.—Medium smooth.

*Fruiting wood*.—Smooth, immature winter color — Pantone Amber Gold 16-1139; immature summer color — Pantone Nile 14-0223.

*Internode length range*.—15-22 mm range, average 18 mm.

*Surface texture of new wood*.—Smooth.

*Mature canes*.—Circular, 20 mm width.

*Time of beginning of leaf bud burst* (*include location(s)*).—April 15 (Grand Junction, Mich.).

*Time of beginning of flowering* (*include location(s)*).—April 25 (Grand Junction, Mich.).

*Time of fruit ripening* (*include location(s)*).—July 28 (Grand Junction, Mich.).

*Disease resistance/susceptibility*.—None claimed.

Foliage:

*Leaf color*.—Upper — Pantone Peridot 17-0336; lower — Pantone Piquant Green 17-0235.

*Leaf arrangement*.—Alternate.

*Leaf margins*.—Smooth.

*Leaf venation*.—Pinnate.

*Leaf apices*.—Acute.

*Leaf bases*.—Acute.

*Vein and petiole colouration*.—Pantone Jade Lime 14-0232.

*Petiole length*.—2 mm.

*Leaf dimensions*.—Overall shape: 60 mm-68 mm range, average 65 mm. Width: 30 mm-35 mm range, average 32 mm.

*Leaf margins*.—Entire; no visible pubescence or nectaries.

*Leaf surface*.—Upper — a few white hairs on midrib (visible 30× microscope); lower — none.

Flower:

*Flower shape*.—Elongate urceolate.
*Flower bud number*.—Medium high.
*Flowers per cluster*.—4-7, avg 6.
*Flower fragrance*.—Light floral.
*Corolla color*.—Pantone Turtle Dove 12-5202.
*Corolla length*.—8 mm.
*Corolla aperture width*.—4 mm.
*Flower peduncle*.—16 mm.
*Color*.—Pantone Willow Green 15-0525.
*Flower pedicel*.—7 mm.
*Color*.—Pantone Willow Green 15-0525.
*Calyx* (*with sepals*).—2 mm.
*Color*.—Pantone Willow Green 15-0525.
*Stamen*.—Length: 7 mm.
*Number per flower*.—10.
*Filament color*.—Pantone Caramel 16-1439.
*Style*.—8 mm.
*Color*.—Pantone Moss 16-0532.
*Pistil*.—6 mm, top of ovary to stigma tip.
*Ovary color*.—Pantone Moss 16-0532.
*Anther*.—Length: 3 mm.
*Number*.—10.
*Color*.—Pantone Caramel 16-1439.
*Pollen*.—Abundance: high.
*Color*.—Pantone Vanilla 12-0712.

Fruit:

*Date of* 50% *maturity*.—July 28 (Grand Junction, Mich.).
*Yield*.—6-7 lbs/bush.
*Berry color*.—With wax: Pantone Cerulean 15-0420, SpectraMagic (L, a, b) 43.17, 0.87, −3.23. With wax removed: Pantone Majolica Blue 19-4125.
*Berry flesh color*.—Pantone Frozen Dew 13-0513.
*Berry surface wax abundance*.—Medium-heavy, persistent.
*Calyx*.—Width — 5 mm; depth — 2 mm; shape — 5 lobed; slight ridging of lobes, pointed inward.
*Berry weight*.—2.7 grams/berry.
*Berry size diameter*.—18 mm width, 13 mm height, Aspect (H/W) — 0.7.
*Berry shape*.—Oblate.
*Cluster density*.—Loose.
*Detachment force*.—Easy.
*Self-fruitfulness*.—Good; cross pollination will enhance maximum yield and size.
*Fruit stem scar*.—Very small, <1 mm, dry.
*Berry firmness*.—Firm; FirmTec2 reading — 260 g/mm$^2$.
*Berry sweetness*.—Medium, high Brix° 13.6.
*Berry acidity*.—Medium, TA — 0.84.
*Berry flavor and texture*.—Very good flavor with balanced sweetness and acidity, crunchy and juicy.
*Suitability for mechanical harvesting*.—Very good due to firm fruit, bush shape, crown size, cluster density.

Seed:

*Seed abundance in fruit*.—Medium 15-20/fruit.
*Seed color*.—Pantone Sunflower 176-1054.
*Seed dry weight*.—NA.
*Seed size*.—1 mm.

Possible typical market uses: Fresh market, processing into jams, puree, yogurt.

Storage quality: Outstanding, 6+ weeks in refrigerated storage.

What is claimed is:

1. A new and distinct cultivar of Blueberry plant named 'BB05-251MI-14' as described and shown herein.

* * * * *